(12) United States Patent
Poetsch et al.

(10) Patent No.: US 6,596,890 B1
(45) Date of Patent: Jul. 22, 2003

(54) ALUMINUM ALKYL COMPLEXES AS COCATALYSTS

(75) Inventors: Eike Poetsch, Mühltal (DE); Ludwig Pohl, Darmstadt (DE); Karin Weiss, Bayreuth (DE); Eva Maria Auth, Fulda (DE); Thomas Metzner, Bindlach (DE); Herbert Schumann, Berlin (DE); Corinna Wassermann, Berlin (DE); Michael Frick, Berlin (DE); Bernd Heymer, Berlin (DE); Stefan Schutte, Berlin (DE); Ulf Dümichen, Milzau (DE); Elmar Hecht, Ribnitz-Damgarten (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/199,410

(22) Filed: Nov. 25, 1998

(30) Foreign Application Priority Data

Nov. 29, 1997 (DE) .......................................... 197 53 135

(51) Int. Cl.$^7$ .............................. C07F 5/06; B01J 31/00
(52) U.S. Cl. ........................ 556/175; 556/176; 502/103; 502/117; 526/160; 526/943
(58) Field of Search ................................ 556/175, 176; 502/103, 117

(56) References Cited

FOREIGN PATENT DOCUMENTS

| JP | 62138506 | 6/1987 |
|---|---|---|
| WO | WO94/12278 | 6/1994 |

OTHER PUBLICATIONS

Jochanan Blum et al., "Palladium–Catalyzed Methylation of Aryl and Vinyl Halides by Stabilized Methylaluminum and Methylgallium Complexes", J. Orig. Chem., 1997, 62, pp. 8681–8686.

Ulf Dumichen et al., "Darstellung und Molekulstruktur von Bis(3–dimethylaminopropylalan)", Journal of Organometallic Chemistry 495 (1995), pp. 71–75.

L. Pohl et al., "Physical Properties of Non–Pyrophoric Group III Precursors for MOVPE", Journal of Crystal Growth 107 (1991), pp. 309–313.

Janusz Lewinski et al., "Structure Characterisation of the Organoaluminium Intermediate Resulting from the Alkylation of Chelated Carbonyl Group. Molecular Structure of Trinuclear [MeAl][C12H20O4][AlMe2]2 Compound", Journal of Organometallic Chemistry 560 (1998), pp. 89–94.

Jochanan Blum et al., "Kinetic Resolution of Racemic 2,2'–bis(trifluoromethanesulfonyloxy)–1,1'–Binaphthalene by Chiral Dimethylaluminum Reagents in the Presence of a Chiral Pd Catalyst", Tetrahedron Leters 39 (1998) pp. 5611–5614.

Christian Boker et al., "Halides of o–Substituted Aryl–Aluminum Compounds with Coordination Numbers Four and Five", XP–002096900, Institute of Inorganic Chemistry, Main Group Met. Chem. (1998), 21(9), pp. 565–579.

Primary Examiner—Porfirio Nazario-Gonzalez
(74) Attorney, Agent, or Firm—Millen White Zelano & Branigan

(57) ABSTRACT

Organometallic aluminum compounds of the general formula (I)

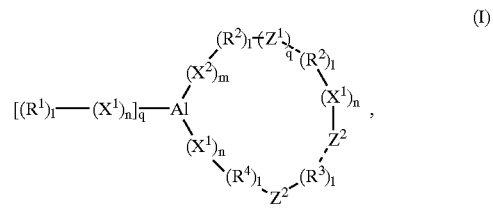

where $X^1$ is NH, $NH_2$*, NH—A*, N—A, $N(A)_2$*, O, OA*, O-Aryl*, S, SA*, P, $P(A)_2$* or a single bond, $X^2$ is NH, N—A, O, S, PA or $X^1$ coordinated to $Al(R^1)_3$, or a single bond, $R^1$ is H; Hal if n=0; A which may be covalently bound to Al; $Si(A)_3$ if $X^1$=O, $R^2$ is A or divalent aryl groups defined note particularly below or divalent unsaturated aliphatic groups defined more particularly below, $R^3$ and $R^4$ are, independently of one another, a bond or $R^2$ or $Si(A)_3$ or $Si(A)_2$, $Z^1$ is a bond or H bound to $R^2$, $Z^2$ is a bond or H bound to $R^2$ or $R^3$, A is branched or unbranched $C_1$–$C_7$-alkyl, $C_1$–$C_7$-alkylidene or $C_1$–$C_7$-alkenylidene, Aryl is phenyl, naphthyl, Hal is F, Cl, and, independently of one another, n, m, p and l are 0 or 1 and q is 1 or 2, where $\Sigma$l+m+n$\geq$3.

9 Claims, No Drawings

ALUMINUM ALKYL COMPLEXES AS COCATALYSTS

The present invention relates to organometallic aluminium compounds of the general formula (I)

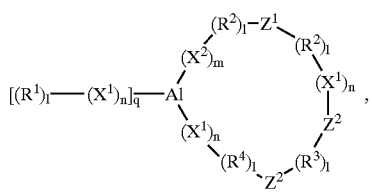

where $X^1$ is NH, $NH_2$*, NH—A*, N—A, $N(A)_2$*, O, OA*, O-Aryl*, S, SA*, P, $P(A)_2$* or a single bond, $X^2$ is NH, N—A, O, S, PA or $X^1$ coordinated to $Al(R^1)_3$, or a single bond, $R^1$ is H; Hal if n=0; A which may be covalently bound to Al; $Si(A)_3$ if $X^1$=O, $R^2$ is A which may be covalently bound to Al; $CH_2$—CH=CH, $CH_2$—C≡C when $Z^1$=H;

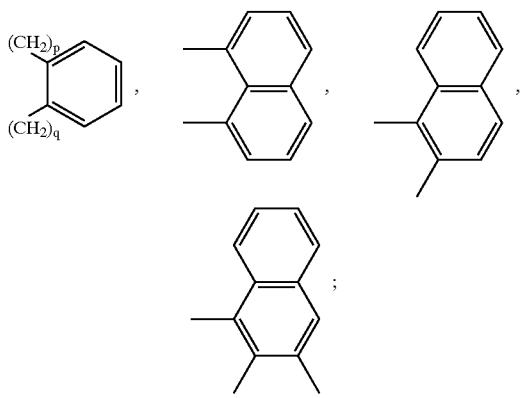

$R^3$ and $R^4$ are, independently of one another, a bond or $R^2$ or $Si(A)_3$ or $Si(A)_2$, $Z^1$ is a bond or H bound to $R_2$, $Z^2$ is a bond or H bound to $R^2$ or $R^3$, where A is branched or unbranched $C_1$-$C_7$-alkyl, $C_1$-$C_7$-alkylidene or $C_1$-$C_7$-alkenylidene, Aryl is phenyl, naphthyl, Hal is F, Cl, and, independently of one another, n is 0, 1, m is 0, 1, p is 0, 1, q is 1, 2 and l is 0, 1, where coordinative bonds can exist between $X^1$, $X^2$ and Al, and $R^1$, $R^2$, $R^3$, $R^4$, $X^1$, $X^2$, $Z^1$ and $Z^2$ can each, independently of one another, take on any of the above meanings at different positions in the molecule and $X^1$ can only take on the meanings denoted by "*" if l=0 and $R^1$, $R^2$, $R^3$ or $R^4$ are not present, which can serve as cocatalysts in olefinic polymerization reactions. In particular, these compounds having improved properties can be used for preparing new Ziegler-Natta catalysts or new coordination catalyst systems which have high activities even at low temperatures and a pressure of about 10 bar.

Customary coordination catalyst systems are extraordinarily diverse catalysts which are used in chemical reactions of and with olefinically unsaturated compounds. These include, in particular, processes for preparing olefin polymers by coordination polymerization and the metathesis of alkenes or alkynes. Processes of substantial industrial importance are the preparation of various polyethylenes for different applications, e.g. high density polyethylene (HDPE) or polyethylene having a particularly low density (linear low density polyethylene, LLDPE) and of polymers and copolymers of ethylene, propylene or other 1-alkenes and alkynes. Catalysed metathesis makes it possible to prepare relatively highly unsaturated hydrocarbon compounds in a targeted manner from unsymmetrical alkenes or alkynes and to obtain long-chain unsaturated hydrocarbons from unsaturated cyclic hydrocarbon compounds. The long-chain unsaturated hydrocarbons are employed, for example, in the preparation of elastomers. In addition, coordination catalysts are employed in further reactions, for instance in alkene hydrogenation or in organometallic syntheses.

On the basis of present-day scientific knowledge of the mechanism of action of coordination catalysts, it is assumed that in each case a transition metal compound forms the catalytically active centre to which the olefinically unsaturated compound is coordinated in a first step. Olefin polymerization proceeds via coordination of the monomers and a subsequent insertion reaction into a transition metal-carbon or transition metal-hydrogen bond. The presence of organometallic compounds in the coordination catalyst systems or during the catalyzed reaction is necessary to activate the catalyst or maintain its activity by reduction and possibly alkylation or formation of a complex system (cation/anion). These compounds are therefore also known as cocatalysts. The compound containing the catalytically active transition metal atom is known as the primary catalyst or precatalyst.

In recent years, coordinative polymerization using complex initiator systems has achieved great industrial importance, particularly for the polymerization of ethylene at low pressures. In the USA alone, over $8 \times 10^9$ metric tons of PE were produced in 1995 (S. W. Bigger; Eur. Polym. J. Vol. 32, No. 4, pp 487, 1996).

The industrially most important catalysts in this field are the Ziegler-Natta catalysts. These are systems consisting of a combination of compounds of metals of transition groups IV–VII of the Periodic Table of the Elements with, for example, alkyl compounds, aryl compounds or hydrides of the elements of main groups I–III. Typical Ziegler catalysts are formed, for example, in the reaction of $TiCl_4$ with $Et_3Al$ or of $TiCl_3$ with $AlEt_2Cl$. These systems are heterogeneous catalysts; they are obtained as a fine suspension in an organic solvent (e.g. heptane).

The most important aluminium alkyls which are preferably used are $AlEt_3$, $Al$-$i$-$Bu_3$, $AlEt_2Cl$, $AlEtCl_2$, and $AlEt_2OR$, all very sensitive to oxygen and moisture in the atmosphere and therefore difficult to handle. In place of the titanium chlorides, compounds of vanadium and chromium are of particular interest, in specific applications also molybdenum, cobalt, rhodium and nickel. In place of the aluminium alkyls, numerous other organometallic compounds of, in particular, sodium, lithium and cadmium have been described as effective in combination with titanium compounds (H. J. Sinn et al., Polymerisation und Insertionsaktivität von Aluminiumtrialkylen und Ziegler-Natta Katalysatoren, Angew. Chem. 72 (1960) 522).

An example of an industrially important solution polymerization process for preparing HDPE is the Dow process. Here, a mixture of $TiCl_x$ and $AlR_3$ in hydrocarbons ($C_8$–$C_9$) is prepared at a pressure p>10 bar and a reaction temperature T>180° C. The activity in the continuous process (140° C., 30 bar; $TiCl_4:AlR_3=1:5$) is 6323 g of PE/h. (Dow, U.S. Pat. No. 3,491,073, 1970).

In a process patented by Du Pont, Ti/V halides are combined with $AlR_3$ in cyclohexane at pressures of 200 bar and a temperature of 180–270° C. The activity is 20–50 kg of PE/g of metal×hour and the viscometrically determined molar mass is $M_n=1.8\times10^5$ g/mol. (Du Pont, U.S. Pat. No. 2,862,917, 1958; J. P. Forsman, Hydrocarbon Processing, 51(11), 130 (1972).

An example of an industrially important suspension polymerization process for preparing HDPE is the Mitsubishi process. Here, HDPE is produced using a titanium catalyst in n-hexane at 5–10 bar and 30–90° C. in a stirred reactor. (A. Kageyama, Hydrocarbon Processing 51(7), 115(1972)). Another example is the Montedison process, which is carried out using titanium catalysts in petroleum spirit at 1–15 bar and 50–100° C. in a stirred reactor. The activity is 200 kg of PE/g of Ti. (A. Heath, Chemical Engineering (April 3) 66(1972).

A further important supplier of HDPE is Hoechst. A heterogeneous catalyst (titanium/support) is used together with aluminium trialkyls in hexane at 8–10 bar and 80–90° C. in a stirred reactor for producing polyethylene. (Kreuter, Chemical Engineering (August 5) 62 (1972)).

After, in the initial phase, this heterogeneity had been held primarily responsible for the catalytic activity ("catalytic surface"), soluble (homogeneous) systems which had approximately the same effectiveness were subsequently found.

Thus, a homogeneous Ziegler catalyst is formed, for example, by combining bis(cyclopentadienyl)titanium dichloride ($cp_2TiCl_2$) or vanadyl chloride ($VOCl_3$) with diethylaluminium chloride ($Et_2AlCl$) or aluminoxane ($[-OAl(CH_3)-]_n$). A further important homogeneous catalyst system is: $cp_2ZrMe_2$/aluminoxane (homogeneous).

$TiCl_4$ on $MgCl_2$ catalyst systems were discovered in 1970 and are referred to as second generation catalyst systems. An example of this heterogeneous system is: $MgCl_2/AlR_3/TiCl_4$. The catalyst activity is 200 kg of PE/g of Ti×h. (A. D. Jenkins, A. Ledwith; Reactivity, Mechanism and Structure in Polymer Chemistry).

All these known catalyst systems have the disadvantages that they can be used only at elevated temperature and a pressure above 10 bar and, despite this, a satisfactory catalyst activity is not achieved in all cases.

The practical use of these catalysts and related types in the wide range of process variants which have been developed can give products which sometimes have very different properties. In the case of olefin polymers which are of generally known importance as materials, useability and field of application depend, because of the properties, firstly on the type of monomers employed or selection and ratio of comonomers and the typical physical properties which characterize the polymer, e.g. mean molar mass, molar mass distribution, degree of branching, degree of crosslinking, crystallinity, density, presence of functional groups in the polymer, etc., secondly on the properties determined by the process, e.g. content of low molecular weight impurities and presence of catalyst residues, and finally on the costs.

Decisive factors for judging the performance of a coordination catalyst system are not only the realization of the desired product properties but also further aspects such as activity of the catalyst system, i.e the amount of catalyst required for economical conversion of a prescribed amount of olefin, the amount of product produced per unit time and the product yield, the loss of catalyst and the reuseability of the catalyst. For this reason, catalyst systems having as high as possible a productivity but also a high specificity for a low degree of branching and a high stereoregularity of the polymer are sought.

However, another important factor is the stability and handleability of the catalyst or its components. Virtually all known coordination catalysts are extremely sensitive to air and moisture. Exposure to (atmospheric) oxygen and/or water reduces or irreversibly destroys the activity of coordination catalysts. Coordination catalysts therefore have to be strictly protected from exposure to air and moisture during their preparation, storage and use, which naturally makes handling more difficult and increases costs.

Customary catalyst systems are also sensitive to materials containing electron-rich elements in the molecule, e.g. oxygen or nitrogen. Compounds such as alcohols and amines or polar monomers which may be of interest as comonomers or additives for the polymer deactivate the catalyst.

Even more sensitive in this respect and therefore even more difficult to handle are the organometallic compounds used as activators or cocatalysts, in particular the aluminium alkyl compounds which are predominantly used for this purpose. Owing to their extreme sensitivity and spontaneous flammability, it is precisely these which present a serious problem in practice.

It is therefore an object of the present invention to find organometallic aluminium compounds which are less sensitive but are nevertheless suitable as activating components in cocatalyst systems and have at least the same, but in particular improved, use properties when employed in these catalyst systems. Furthermore, these compounds should have a lower sensitivity and thus be easier to handle.

This object is achieved by new compounds of the general formula (I)

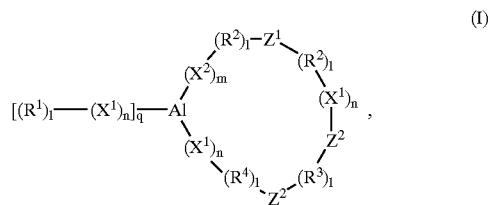

where
$X^1$ is NH, $NH_2*$, NH—A*, N—A, $N(A)_2*$, O, OA*, O-Aryl*, S, SA*, P, $P(A)_2*$ or a single bond,
$X^2$ is NH, N—A, O, S, PA or $X^1$ coordinated to $Al(R^1)_3$, or a single bond,
$R^1$ is H; Hal if n=0; A which may be covalently bound to Al; $Si(A)_3$ if $X^1=O$,
$R^2$ is A which may be covalently bound to Al; $CH_2$—CH=CH, $CH_2$—C≡C when $Z^1$=H;

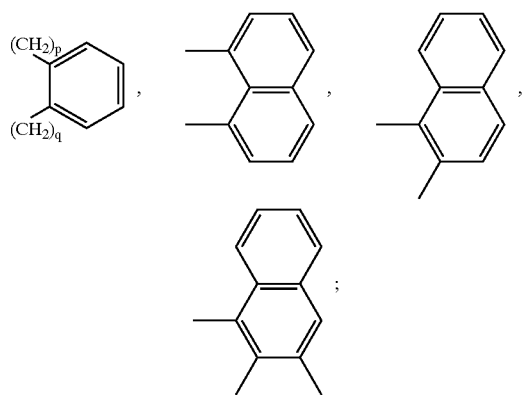

$R^3$ and $R^4$ are, independently of one another, a bond or $R^2$ or $Si(A)_3$ or $Si(A)_2$, $Z^1$ is a bond or H bound to $R^2$, $Z^2$ is a bond or H bound to $R^2$ or $R^3$, where A is branched or unbranched $C_1$-$C_7$-alkyl, $C_1$-$C_7$-alkylidene or $C_1$-$C_7$-alkenylidene, Aryl is phenyl, naphthyl, Hal is F, Cl, and, independently of one another, n is 0, 1, m is 0, 1, p is 0, 1, q is 1, 2 and l is 0, 1, where coordinative bonds can exist between $X^1$, $X^2$ and Al, and $R^1$, $R^2$, $R^3$, $R^4$, $X^1$, $X^2$, $Z^1$ and $Z^2$ can each, independently of one another, take on any of the above meanings at different positions in the molecule and $X^1$ can only take on the meanings denoted by "*" if l=0 and $R^1$, $R^2$, $R^3$ or $R^4$ are not present.

It has been found that intramolecularly stabilized organometallic aluminium compounds of the formula (I) are very useful as components in coordination catalyst systems.

The present invention accordingly provides for the use of intramolecularly stabilized organometallic aluminium compounds of the formula (I) as components in coordination catalyst systems and provides coordination catalyst systems comprising compounds of the general formula (I).

In particular, the invention provides for the use of compounds of the formula (I) as components in Ziegler-Natta catalysts.

Coordination catalyst systems comprising compounds of the general formula (I) are, according to the invention, in the form of combinations with transition metal compounds of transition groups IV to VIII of the Periodic Table of the Elements.

Combinations according to the invention of coordination catalyst systems comprising compounds of the general formula (I) with transition metal compounds are, in particular, those in which compounds selected from the group consisting of $TiCl_4$ and $VCl_4$ are present.

The invention also provides processes for preparing polymers by polymerization, in which the abovementioned coordination catalyst systems are used. In particular, these are processes for preparing polyethylene, preferably processes for preparing high molecular weight polyethylene.

Compounds of the formula (I) according to the invention can have a cyclic structure in which aluminium as an element of group IIIa of the Periodic Table of the Elements is in each case a member of the ring system. However, they can also be compounds in which the various organic radicals are, independently of one another, covalently bound or coordinated to the aluminium atom. In compounds of the formula (I) which have no cyclic structure, aluminium is in each case the central atom of the organometallic compound.

In both cyclic and non-cyclic compounds of the formula (I), atoms directly adjacent to the aluminium can be carbon, nitrogen, oxygen, sulfur or phosphorus atoms. Of these atoms adjacent to the aluminium, at least one can be coordinated to aluminium. Such adjacent atoms can be substituted by one or two alkyl, alkenyl or aryl groups. In the case of different substitution and additional coordination via O, N, S or P atoms, the central aluminium atom becomes a centre of chirality. The chiral centre makes possible stereocontrolled polymerizations and copolymerizations, for example of propylene.

Alkenyl or alkyl substituents can be linear or branched and have 1–7 carbon atoms. They can also be part of a ring. Preference is given to alkenyl and alkyl groups having 1–6 carbon atoms selected from the group consisting of methyl, ethyl, n- and i-propyl, 2-propenyl, 2-propynyl, n-, 2- and t-butyl, 2- and 3-butenyl, 1,3-butadienyl, n-, 2- and 3-pentyl, 2,2-dimethylpropyl, 2-methylbutyl, 3-methylbutyl, 2-, 3- and 4-pentenyl, 1,3-, 1,4- and 2,4-pentadienyl, n-, 2- and 3-hexyl, 2- and 3-methylpentyl, 2,2- and 3,3-dimethylbutyl and 2-ethylbutyl; particular preference is given to unbranched alkyl and alkenyl groups. Such alkyl groups are represented by the symbol A in formula (I). In the case of cyclic compounds, preference is given to those having 5- and 6-membered ring systems in which aluminium is integrated into the ring.

Suitable aryl substituents are phenyl and naphthyl. Aryl substituents are preferably part of the ring. They can be bound directly or via alkyl spacers to hetero atoms such as N, O, S or P which form a covalent or coordinate bond to the aluminium. However, they can also be bound directly to the aluminiun atom.

Hydrogen, halogen atoms or trialkylsilyl radicals can also be bound to atoms which are adjacent to the aluminium and are not part of the ring. Suitable halogen atoms are fluorine and chlorine, preference being given to chlorine. Particular preference is given to hydrogen atoms. Other suitable aluminium compounds are those in which a halogen atom, preferably a chlorine atom, is bound to aluminium. In this case, an alkyl radical, preferably having 1–4 carbon atoms, can be bound as further non-ring substituent to the aluminium atom. According to the invention, compounds containing trialkylsilyl radicals have these bound to aluminium via an oxygen atom.

Good coordination catalyst properties are achieved by the use of compounds of the formula (I) in which n in one case assumes the value 0 and $Z^2$, $R^3$ and $R^4$ are a bond, $R^2$ is an unsaturated group selected from among $CH_2$—$CH$=$CH$ and $CH_2$—$C\equiv C$ and $Z^1$ is H bound to $R^2$.

Particularly good coordination catalyst properties are displayed by systems in which an aromatic ring such as phenyl or naphthyl is integrated into the aluminium-containing ring of the compounds of formula (I), either via hetero atoms which are part of the ring or via alkyl groups which serve as spacer between the aluminium atom and the aromatic ring.

Compounds according to the invention also include those in which at least one coordinate bond to a further organoaluminium compound is present. This further organoaluminium compound can be a simple trialkylaluminium compound or an identical compound.

Suitable compounds of the formula (I) have four substituents on a central aluminium atom, of which very probably at least one is coordinated and contributes to stabilization of the compound.

Compounds according to the invention can be prepared by the methods known to those skilled in the art for preparing organometallic compounds. Methods of preparing such compounds are described, for example, in G. Bähr, P. Burba, Methoden der organischen Chemie, Vol. XIII/4, Georg Thieme Verlag, Stuttgart (1970). These compounds can be prepared under the reaction conditions which are known and suitable for the reactions mentioned. However, use can also be made of variants which are known per se and are not described in more detail here. Further details of the synthesis may be found in DE 38 17 090 A1 and DE 37 26 485 A1 or Chem. Ber. 124, 1113–1119, (1971).

It has surprisingly been found that the compounds of the invention are quite stable to oxygen, in particular air, and moisture. This also applies to coordination catalysts prepared using these compounds. Furthermore, corresponding coordination catalyst systems have a particularly high stability under reaction conditions. They are significantly less susceptible to deactivation by compounds having free electron pairs, in particular compounds containing hetero atoms such as sulfur, oxygen or nitrogen. These catalyst systems have very particularly advantageous properties in polymerization reactions, in particular olefin polymerization reactions.

Thus, it has been found that the use of compounds according to the invention in coordination catalyst systems in which transition metal compounds of transition groups IV and VIII, in particular compounds of titanium and of vanadium, are employed leads to particularly good polymerization results. Indeed, both catalyst systems having a particularly high activity and polymerization products having high molecular weights and at the same time a uniform structure are obtained. Particularly advantageous properties are here offered by the compounds of the invention which contain one or two hetero atoms. For example, high molecular weight products having molecular weights of $M_n > 10^6$ are obtained in the polymerization of ethylene. Very particularly good results are achieved using corresponding $VCl_4$ catalyst systems. Particularly good results are achieved by systems in which $VCl_4$ is activated by cyclic aluminium alkyls in which a nitrogen or oxygen atom is located next to the aluminium atom in the ring and, optionally, an aromatic ring is part of the aluminium-containing ring. Excellent activity increases are achieved by the compounds designated as AlO2 and AlN10 in Table 1, which give high molecular weight products in high yields both in the presence of $TiCl_4$ and with $VCl_4$.

All catalyst systems give very high molecular weight polyethylene. This means that during the polymerization there is a low level of reactions which break the polymer chains from the catalytic centre.

Overall, the coordination catalyst systems of the invention display a particularly high specificity in olefin polymerization and give products having high molar masses and narrow molar mass distributions. Although this is also dependent on the way in which the reaction is carried out and on the reactants used, it is standard procedure for a person skilled in the art to optimize the reaction conditions as necessary.

The use according to the invention of the compounds of formula (I) as activating components in coordination catalyst systems is fully analogous to and a replacement for the use of the hitherto customary organometallic compounds, in particular the relatively unstable and hazardous aluminium alkyls.

The high activity of the catalyst systems enables more product to be formed using a given amount of catalyst, or the amount of catalyst can be significantly reduced. A consequence of the latter is that less catalyst has to be separated from the product and also that significantly less catalyst remains in the product. In addition, the costs can be reduced because of a lower catalyst consumption. Although the costs are influenced by a series of other factors such as qualitative and quantitative composition of the catalyst systems, monomers used, reaction conditions and method of operation in the polymerization, the catalyst used can play a not inconsiderable role, even if only in terms of protective measures required for maintaining the activity. Owing to the wide variety of organoaluminium compounds of the invention, a person skilled in the art can readily determine and optimize the most suitable catalyst system for his purposes by means of routine experiments.

As has already been stated above, the compounds of the invention having the formula (I) are relatively stable compounds which advantageously give likewise stable coordination catalyst systems, thus making their preparation, storage and use significantly less problematical than is the case for systems known hitherto.

The preparation and use of the catalysts is carried out in a manner known per se, as is customary for the respective system and the respective use. In general, olefin polymerization and metathesis using heterogeneous catalysis are carried out in the gaseous or liquid phase. If necessary, a supported precatalyst is first prepared from the catalytic transition metal compound and a support material and this is activated or preactivated if necessary in a customary manner and then, if appropriate, suspended in a solvent, e.g. in a hydrocarbon such as pentane, hexane or toluene. The addition of the cocatalyst is carried out, as is also otherwise customary, immediately before reaction of the monomers or in situ in the presence of the latter. The control of the reaction and the isolation and work-up of the reaction product is likewise carried out in a fully analogous way.

As has already been mentioned above, the increased stability of the organoaluminium compounds and the considerably reduced sensitivity of the catalyst compounds obtained makes all process steps significantly easier and enables them to be carried out under significantly less stringent protective and safety measures.

The present invention therefore makes available new catalyst systems which have advantageous properties and can also be tailored to the particular needs of the application.

The following examples illustrate the present invention. However, they do not restrict the subject-matter of the invention to the examples given and a person skilled in the art will be able to see the wider applicability of the invention on the basis of the information disclosed.

EXAMPLES

Example 1

An autoclave is evacuated to a high vacuum of $5 \times 10^{-3}$ for one hour, subsequently filled with argon and thermostatted to the reaction temperature of 30° C. 480 ml of heptane are introduced as solvent and thermostatted for about 15 minutes until the temperature in the autoclave is constant at the desired value.

At the same time, the catalyst solution is prepared in a swivel flask. 403 mg of cocatalyst $AlOO_4$ (194.21 g/mol) (the chemical structure of this cocatalyst is shown in the table), corresponding to a five-fold excess based on $VCl_4$ are placed in the flask together with 20 ml of solvent. While stirring vigorously, 80 mg of $VCl_4$ dissolved in hexane (0.5 ml of a 0.83 molar solution of $VCl_4$ in hexane) are then added dropwise, immediately giving a brownish black precipitate. After stirring for 10 minutes, this mixture is introduced into the thermostatted autoclave.

The catalyst solution is mixed with the solvent in the autoclave by stirring for another 50 seconds at a stirrer speed of 700 revolutions per minute before the ethylene is injected into the autoclave through a pressure valve at a pressure of 10 bar.

The reaction is stopped after one hour by venting the overpressure and enabling access of air.

The solvent is decanted from the polyethylene formed and the product which remains is washed with methanol. The solution which has been decanted off is analysed for low molecular weight constituents by gas chromatography.

The product obtained is a fine, white polyethylene powder.

The reaction can also be carried out using toluene as solvent.

| Catalyst | Experimental results: | |
|---|---|---|
| | Polyethylene yield | Catalyst activity |
| $AlOO_4$ | 110 g | 8.7 kg PE/g V h |
| Comparison: $AlO_2$ in heptane | 90 g | 7.0 kg PE/g V h |

Further experimental results which were obtained under identical or similar conditions are summarized in Table 1. This table also contains experiments which were carried out in the presence of an aluminium cocatalyst according to the invention and $TiCl_4$ as catalyst.

TABLE 1

Reaction conditions:

| | |
|---|---|
| Ethylene pressure: | 10 bar |
| Reaction temperature: | 30° C. |
| Reaction time: | 60 minutes |
| Catalyst concentration: | $TiCl_4$: 5.3 $10^{-4}$ mol/l |
| | $VCl_4$: 8.3 $10^{-4}$ mol/l |
| Catalyst/cocatalyst ratio | 1.5 |
| Solvent volume | 500 ml |

Abbreviations:

| | | | |
|---|---|---|---|
| Solvent | SOL | Heptane | H |
| | | Toluene | T |
| Activity | A [kg PE/g Ti(V) h] | | |
| No reaction | nR | | |
| Melting point | $T_M$ [° C.] (DSC, 2nd run) | | |
| Molar mass | $M_\eta$ [g/mol] | measured viscometrically in decalin at 135° C. and determined from a PE calibration curve (c = 0.03 g/dl) | |

*[1] Reaction occurs only at 50° C.
*[2] No reaction even at 50° C. and doubled concentration
*[3] Reaction stopped after 250 s
*[4] Reaction stopped after 1850 s
*[5] Reaction stopped after 500 s
*[6] Reaction stopped after 30 min
*[7] Reaction occurs only at 50° C. and doubled concentration; reaction stopped after 10 min
*[8] No reaction even at 50° C.

| | | TiCl₄ | | | | VCl₄ | | | |
|---|---|---|---|---|---|---|---|---|---|
| | Aluminium alkyl | SOL | A | $T_M$ | $M_\eta \, 10^6$ | SOL | A | $T_M$ | $M_\eta \, 10^6$ |
| AlN1 | 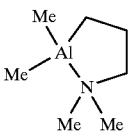 | H<br>T | 4.7<br>0.8 | 135<br>n.d. | 2.5<br>n.d. | H<br>T | 4.6<br>1.1 | 134<br>139.1 | 6.5<br>2.2 |
| AlN4 | 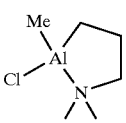 | H<br>T | nr<br>0.8*[1]<br>0.3*[1] | —<br>138.3<br>n.d. | —<br>6.5<br>n.d. | —<br>H<br>T | —<br>1.2<br>0.7 | —<br>135.8<br>n.d. | —<br>6.4<br>n.d. |
| AlN2 | 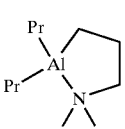 | H<br>T | nr<br>nr*[8] | —<br>— | —<br>— | H<br>T | 2.0<br>0.3 | 134<br>n.d. | 1.8<br>n.d. |
| AlN8 | 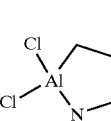 | H<br>T | nr*[8]<br>nr*[8] | —<br>— | —<br>— | H<br>T | 6.1<br>4.2 | 137.5<br>138.6 | 6.3<br>5.0 |
| AlN10 | 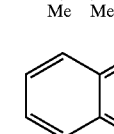 | H<br>T | 0.15*[1]<br>nr*[2] | 135.7<br>— | 1.9<br>— | H<br>T | 69.3*[3]<br>8.7*[4] | 138.2<br>135.6 | 2.9<br>3.7 |

TABLE 1-continued

| Compound | Structure | | | | | | | | |
|---|---|---|---|---|---|---|---|---|---|
| AlO2 | Me-Al(Me)-O-cyclic(Me) | H | nr[*2] | — | — | H | 68.1[*5] | 137.0 | 5.2 |
|  |  | T | 17.5 | 140.4 | 4.2 | T | 5.5 | 138.7 | 4.7 |
| AlN3 | spiro Al cyclohexyl with Me Me | H | 32.2[*6] | 138.7 | 2.9 | H | 17.9 | 135.0 | 8.0 |
|  |  | T | 0.2 | n.b. | n.b. | T | 3.4 | 134.8 | 5.5 |
| AlOO4 | Me2N-O-CH2-aryl-O-Me | H | nr[*2] | — | — | H | 8.0 | 136.1 | 3.5 |
|  |  | T | 3.0 | 140.3 | 4.1 | T | 8.7 | 137.4 | 3.7 |
| AlN'1 | dimer Al-N allyl Me | H | nr[*2] | — | — | H | 8.7 | 135.7 | 3.9 |
|  |  | T | nr[*2] | — | — | T | 1.8 | 136.2 | 4.4 |
| Al(Si)O1 | Me2Al-O-SiMe2- ring | H | nr | — | — | H | nr | — | — |
|  |  | T |  |  |  | T | 21.0[*7] | 139.6 | 2.8 |

[*1]Reaction occurs only at 50° C.
[*2]No reaction even at 50° C. and doubled concentration
[*3]Reaction stopped after 250 s
[*4]Reaction stopped after 1850 s
[*5]Reaction stopped after 500 s
[*6]Reaction stopped after 30 min
[*7]Reaction occurs only at 50° C. and doubled concentration; reaction stopped after 10 min
[*8]No reaction even at 50° C.

TABLE 2

Comparison of Al, Ga and In compounds as cocatalyts in ethylene polymerization. Cocatalysts used can be prepared as described in DE 38 17 090 A1.

M: alkyl = 1:5    Temperature: 30° C.
M = V, Ti          Reaction time: 1 h
Solvent: Heptane   Ethylene pressure: 10 bar

| Cocatalyst | Structure | Metal chloride | Yield [kg PE/gMh] | $M_\mu$ | $T_m$ [° C.] |
|---|---|---|---|---|---|
| Ala10 | Me2Al-pyrrolidinyl-NMe2 | TiCl4 | 4.7 | $2.5 \times 10^6$ | 134 |
| Ga10 | Me2Ga-pyrrolidinyl-NMe2 | TiCl4 | no PE | — | — |
| Ind10 | Me2In-pyrrolidinyl-NMe2 | TiCl4 | no PE | — | — |
| Ala10 | Me2Al-pyrrolidinyl-NMe2 | VCl4 | 0.9 | $6.5 \times 10^6$ | 134 |
| Ga10 | Me2Ga-pyrrolidinyl-NMe2 | VCl4 | 0.12 | $6.3 \times 10^6$ | 134 |

TABLE 2-continued

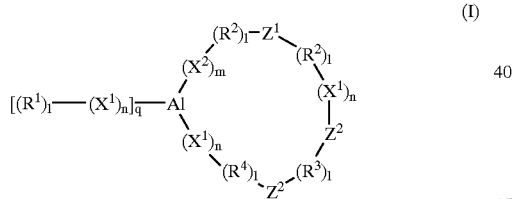

| | | | | |
|---|---|---|---|---|
| Ind10 | (structure) | VCl₄ | 0.05 | 6.6 × 10⁶ — 4.2 |

Results

1. The aluminium cocatalyst has the highest activity.
2. The activity decreases in the order Al, Ga, In compound.
3. The Ga and In cocatalysts used give oligomeric by-products.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The entire disclosure of all applications, patents and publications, cited above and below, and of corresponding German application No. 197 53 135.0, filed Nov. 29, 1997 is hereby incorporated by reference.

What is claimed is:

1. A compound of the general formula (I)

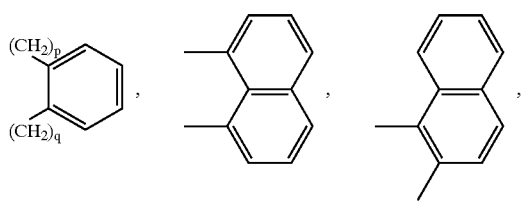

(I)

where $X^1$ is NH, NH₂*, NH—A*, N—A, N(A)₂*, O, OA*, O-Aryl*, S, SA*, P, P(A)₂* or a single bond, $X^2$ is NH, N—A, O, S, PA Or $X^1$ coordinated to Al(R¹)₃, or a single bond $R^1$ is H, Hal if n=0; A which may be covalently bound to Al; Si(A)₃ if $X^1$=O, $R^2$ is A which may be covalently bound to Al; CH₂—CH=CH, CH₂—C≡C when $Z^1$=H;

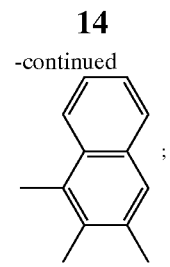

$R^3$ and $R^4$ are independently of one another, a bond or $R^2$ or Si(A)₃ or Si(A)₂, $Z^1$ is a bond or H bound to $R^2$, $Z^2$ is a bond or H bound to $R^2$ or $R^3$, where A is branched or unbranched C₁–C₇-alkyl, C₁–C₇-alkylidene or C₁–C₇-alkenylidene, Aryl is phenyl, naphthyl, Hal is F, Cl, and, independently of one another, each n is 0, 1, m is 0, 1, p is 0, 1, each q is 1, 2, and each l is 0, 1, where Σl+m+n≧3 and where coordinative bonds can exist between $X^1$, $X^2$ and Al, and $R^1$, $R^2$, $R^3$, $R^4$, $X^1$, $X^2$, $Z^1$ and $Z^2$ can each, independently of one another, take on any of the above meanings at different positions in the molecule, and $X^1$ can only take on the meanings denoted by "*" if l=0 and $R^1$, $R^2$, $R^3$ or $R^4$ are not present and where $X^1$ or $X^2$ is O and one of $Z^1$ or $Z^2$ is H, then $R^2$ and $R^3$ are not branched or unbranched C₁–C₄-alkyl.

2. A method of using the compounds of the general formula (I) below, which comprises incorporating said compounds as components in coordination catalyst systems,

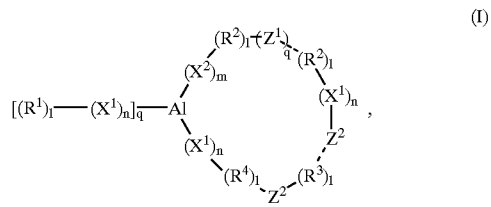

(I)

where $X^1$ is NH, NH₂, NH—A, N—A, N(A)₂, O, OA, O-Aryl, S, SA, P, P(A)₂ or a single bond, $X^2$ is NH, N—A, O, S, PA Or $X^1$ coordinated to Al(R¹)₃, or a single bond $R^1$ is H, Hal if n=0; A which may be covalently bound to Al; Si(A)$_3$ if $X^1$=O, $R^2$ is A which may be covalently bound to Al; $CH_2$—$CH$=$CH$, $CH_2$—$C$≡$C$ when $Z^1$=H;

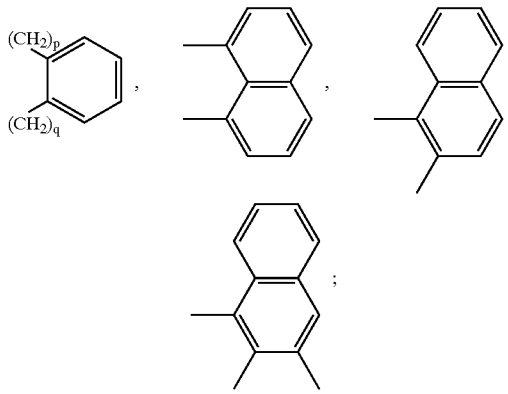

$R^3$ and $R^4$ are independently of one another, a bond or $R^2$ or Si(A)$_3$ or Si(A)$_2$, $Z^1$ is a bond or H bound to $R^2$, $Z^2$ is a bond or H bound to $R^2$ or $R^3$, where A is branched or unbranched $C_1$–$C_7$-alkyl, $C_1$–$C_7$-alkylidene or $C_1$–$C_7$-alkenylidene, Aryl is phenyl, naphthyl, Hal is F, Cl, and, independently of one another, each n is 0, 1, m is 0, 1, p is 0, 1, each q is 1, 2, and each l is 0, 1, where Σl+m+n≧3 and where coordinative bonds can exist between $X^1$, $X^2$ and Al, and $R^1$, $R^2$, $R^3$, $R^4$, $X^1$, $X^2$, $Z^1$ and $Z^2$ can each, independently of one another, take on any of the above meanings at different positions in the molecule.

3. A method of using the compounds of the general formula (I) below, which comprises incorporating said compounds as components in Ziegler-Natta catalysts

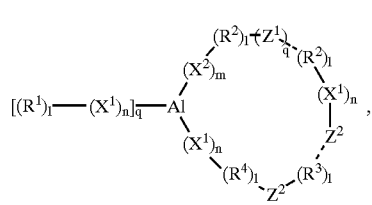

(I)

where $X^1$ is NH, NH$_2$, NH—A, N—A, N(A)$_2$, O, OA, O-Aryl, S, SA, P, P(A)$_2$ or a single bond, $X^2$ is NH, N—A, O, S, PA Or $X^1$ coordinated to Al(R$^1$)$_3$, or a single bond $R^1$ is H, Hal if n=0; A which may be covalently bound to Al; Si(A)$_3$ if $X^1$=O, $R^2$ is A which may be covalently bound to Al; $CH_2$—$CH$=$CH$, $CH_2$—$C$≡$C$ when $Z^1$=H;

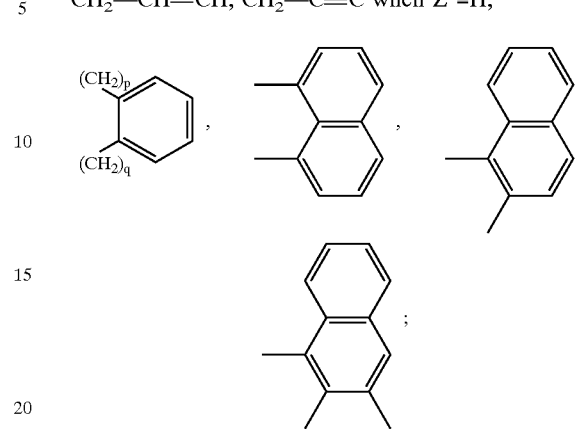

where $X^1$ is NH, NH$_2$, NH—A, N—A, N(A)$_2$, O, OA, O-Aryl, S, SA, P, P(A)$_2$ or a single bond, $X^2$ is NH, N—A, O, S, PA Or $X^1$ coordinated to Al(R$^1$)$_3$, or a single bond $R^1$ is H, Hal if n=0; A which may be covalently bound to Al; Si(A)$_3$ if $X^1$=O, $R^2$ is A which may be covalently bound to Al; $CH_2$—$CH$=$CH$, $CH_2$—$C$≡$C$ when $Z^1$=H;

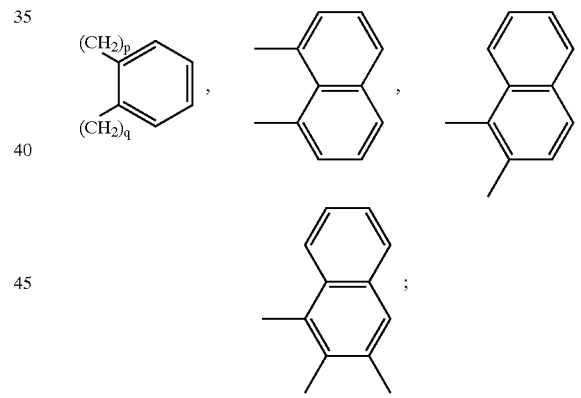

$R^3$ and $R^4$ are independently of one another, a bond or $R^2$ or Si(A)$_3$ or Si(A)$_2$, $Z^1$ is a bond or H bound to $R^2$, $Z^2$ is a bond or H bound to $R^2$ or $R^3$, where A is branched or unbranched $C_1$–$C_7$-alkyl, $C_1$–$C_7$-alkylidene or $C_1$–$C_7$-alkenylidene, Aryl is phenyl, naphthyl, Hal is F, Cl, and, independently of one another, each n is 0, 1, m is 0, 1, p is 0, 1, each q is 1, 2, and each l is 0, 1, where $\Sigma l+m+n \geq 3$ and where coordinative bonds can exist between $X^1$, $X^2$ and Al, and $R^1$, $R^2$, $R^3$, $R^4$, $X^1$, $X^2$, $Z^1$ and $Z^2$ can each, independently of one another, take on any of the above meanings at different positions in the molecule.

4. A compound of the general formula (I)

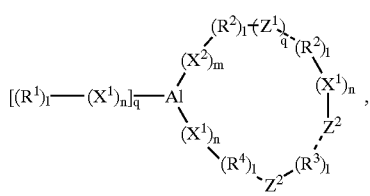

(I)

where $X^1$ is NH, $NH_2$*, NH—A*, N—A, $N(A)_2$*, O, OA*, O-Aryl*, S, SA*, P, $P(A)_2$* or a single bond, $X^2$ is NH, N—A, O, S, PA Or $X^1$ coordinated to $Al(R^1)_3$, or a single bond $R^1$ is H, Hal if n=0; A which may be covalently bound to Al; $Si(A)_3$ if $X^1$=O, $R^2$ is A which may be covalently bound to Al; $CH_2$—CH=CH, $CH_2$—C≡C when $Z^1$=H;

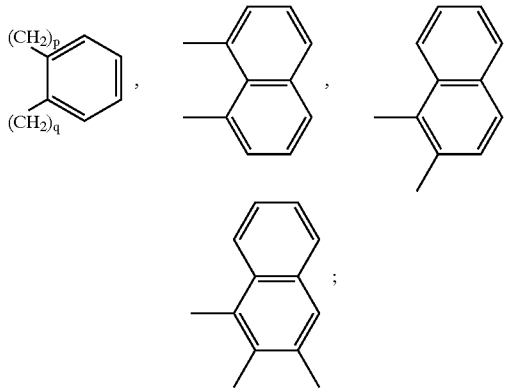

$R^3$ and $R^4$ are independently of one another, a bond or $R^2$ or $Si(A)_3$ or $Si(A)_2$, $Z^1$ is a bond or H bound to $R^2$, $Z^2$ is a bond or H bound to $R^2$ or $R^3$, where A is branched or unbranched $C_1$–$C_7$-alkyl, $C_1$–$C_7$-alkylidene or $C_1$–$C_7$-alkenylidene, Aryl is phenyl, naphthyl, Hal is F, Cl, and, independently of one another, each n is 0, 1, m is 0, 1, p is 0, 1, each q is 1, 2 and each l is 0, 1, where n+l=1 or 2 and m+$\Sigma$ each l in the ring+$\Sigma$ each n in the ring n$\geq$2 and where coordinative bonds can exist between $X^1$, $X^2$ and Al, and $R^1$, $R^2$, $R^3$, $R^4$, $X^1$, $X^2$, $Z^1$ and $Z^2$ can each, independently of one another, take on any of the above meanings at different positions in the molecule and $X^1$ can only take on the meanings denoted by "*" if l=0 and $R^1$, $R^2$, $R^3$ or $R^4$ are not present and where $X^1$ or $X^2$ is O and one of $Z^1$ or $Z^2$ is H, then $R^2$ and $R^3$ are not branched or unbranched $C_1$–$C_4$-alkyl.

5. A compound of claim 1 wherein $\Sigma l+m+n \geq 4$.

6. A compound of claim 1 wherein $\Sigma l+m+n \leq 4$.

7. A compound of one of the formulae below

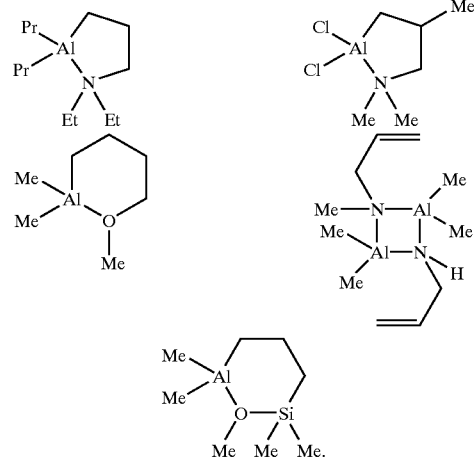

8. A method of using the compounds of claim 7, which comprises incorporating said compounds as components in coordination catalyst systems.

9. A method of using the compounds of claim 7, which comprises incorporating said compounds as components in Zeigler-Natta catalysts.

* * * * *